(12) United States Patent
Wang et al.

(10) Patent No.: US 6,903,230 B2
(45) Date of Patent: Jun. 7, 2005

(54) PROCESS FOR PRODUCING A FLUORINE-CONTAINING COMPOUND

(75) Inventors: Shuzhong Wang, Kanagawa (JP); Kazuhiko Hayashi, Kanagawa (JP); Shinsuke Kaga, Kanagawa (JP); Kazuya Oharu, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/629,710

(22) Filed: Jul. 30, 2003

(65) Prior Publication Data

US 2004/0024269 A1 Feb. 5, 2004

Related U.S. Application Data

(63) Continuation of application No. PCT/JP02/00795, filed on Jan. 31, 2002.

(30) Foreign Application Priority Data

Jan. 31, 2001 (JP) ........................ 2001-024174

(51) Int. Cl.[7] ..................... C07C 19/08; C07C 25/13; C07D 69/76
(52) U.S. Cl. ................. 560/51; 570/123; 570/127; 570/131; 570/134
(58) Field of Search ................. 560/51; 570/123, 570/127, 131, 134

(56) References Cited

U.S. PATENT DOCUMENTS 4,792,618 A * 12/1988 Bieron et al. ............. 560/127
6,080,886 A    6/2000 Lal et al.

FOREIGN PATENT DOCUMENTS

| EP | 0 905 109 | 3/1999 | |
|----|-----------|--------|---|
| JP | 1-199922 | 8/1989 | |
| JP | 6-135869 | 5/1994 | |
| JP | 7-33340 | 4/1995 | |
| WO | WO 96/03357 | 2/1996 | |
| WO | WO96/03357 | * 2/1996 | .................. 560/51 |

OTHER PUBLICATIONS

Frederique Tellier et al., "Introduction Stereoselective Du Groupement Trifluorometiiyle Dans Des Systems Insatures," *Tetrahedron Letters*, vol. 32, No. 42, pp. 5963–5964, 1991.

A. J. Downs, "A Cryoscopic Investigation of the Interaction of Bis(Trifluoromethyl) Mercury with Halide Ions", *J. Inorg. Nucl. Chem.*, 1964, vol. 26, pp. 41–46.

Ernest L. Eliel, et al., "Conformational Analysis. XIII. The Validity of the Nuclear Magnetic Resonance Method of Establishing Conformational Equilibria[1]", Journal of the American Chemical Society, vol. 90, No. 3, XP–002304677, Jan. 31, 1968, pp. 682–689.

C. W. Jefford, et al., "Fluorine NMR. Spectra of Conformationally Constrained Gem–Difluorocyclohexanes", Helvetica Chimica Acta, vol. 53, XP–009039625, 1970, pp. 1184–1194.

* cited by examiner

Primary Examiner—Cecilia J. Tsang
Assistant Examiner—Raymond Covington
(74) Attorney, Agent, or Firm—Oblon, Spivak, McClelland, Maier & Neustadt, P.C.

(57) ABSTRACT

It is to provide a process for synthesizing an intended fluorine-containing compound having a geminal difluoro structure with a high yield, by subjecting a carbonyl compound which is readily available to a two-stage reaction.

A compound (1) such as ethyl 4-oxocyclohexanecarboxylate is reacted with a compound of the formula X-Z or a compound of the formula $Z_2O$ (wherein Z is a monovalent group which gives a leaving group of the structure —OZ, and X is a chlorine atom, a bromine atom or an iodine atom) such as phosphorus pentachloride, and then a fluorinating agent which generates fluorine anions such as HF is acted thereon to obtain a fluorine-containing compound (2) such as ethyl 4,4-difluorocyclohexanecarboxylate

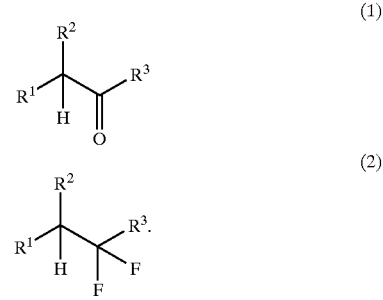

20 Claims, No Drawings

PROCESS FOR PRODUCING A FLUORINE-CONTAINING COMPOUND

TECHNICAL FIELD

The present invention relates to a process for effectively producing a fluorine-containing compound having such a structure that two fluorine atoms are bonded to one carbon atom (—$CF_2$), i.e. a geminal difluoro structure. The fluorine-containing compound of the formula (2) of the present invention is a compound useful as e.g. perfume, pharmaceuticals, agricultural chemicals and chemical agents.

BACKGROUND ART

As a method for introducing a fluorine atom bonded to a carbon atom into a compound, (a) a method of reacting a fluorinating agent which generates fluorine anions (such as KF or HF) with a chlorine atom bonded to a carbon atom to carry out a nucleophilic substitution reaction of $F^-$. As a method for obtaining a fluorine-containing compound having a geminal difluoro structure by means of said method, a method of fluorinating a compound having a geminal dichloro structure (—$CCl_2$ structure) at the corresponding part as a material may be mentioned.

However, it is generally difficult to selectively obtain a desired compound having a geminal dichloro structure to be used for the reaction of (a), and such a method can hardly be employed as an industrial production method, such being problematic. Particularly, when a ketone part of a compound having a C—H structure at the α-position of a ketone is converted to a geminal dichloro structure, a reaction such as elimination of HCl takes place, whereby at least two types of compounds are formed, and it tends to be difficult to obtain an intended compound with a high yield, such being problematic. Accordingly, a method of converting a ketone to a geminal dichloro structure, followed by fluorination, has not been carried out.

Further, as another method of synthesizing a fluorine-containing compound having a geminal difluoro structure by another method, (b) a method of reacting a carbonyl compound or a thiocarbonyl compound with a fluorinated sulfur type fluorinating agent (hereinafter referred to as SF compound) such as $SF_4$ (J. Ing. Nucl. Chem., 1964, 26, 41.) or diethylaminosulfur trifluoride (($CH_3CH_2$)$_2NSF_3$: hereinafter referred to as DAST) (Tetrahedron Lett., 1991, 32, 5963.) has been known. Further, in recent years, a method of employing DAST wherein a substituent on a nitrogen atom is converted (U.S. Pat. No. 6,080,886) has been reported.

However, the SF compound in the method (b) is a compound which requires careful handling, and such a problem that a severe reaction which is difficult to control may occur in the after-treatment has been reported, and application as an industrial production method is difficult, such being problematic. Further, in a case where a reaction is carried out by using the SF compound, removal of HF of the product may take place, whereby a fluoroolefin forms as a by-product, thus decreasing purity of the product. Further, depending upon the substrate used for the reaction, the difference in the boiling point between the fluoroolefin as the by-product and the intended compound is small, whereby a complicated separation operation may be required, or the yield may significantly decrease by the purification operation, such being problematic.

Further, a means to fluorinate a chloroolefin obtained by (c) Diels-Alder reaction with HF has been reported (U.S. Pat. No. 4,792,618). However, compounds to which the method (c) can be applied are limited in structure. Further, in many cases, isomers which are difficult to be separated and purified form as by-products, such being disadvantageous as a method for obtaining a geminal difluoro compound with a high purity.

It is an object of the present invention to overcome the above problems, and to provide a process for synthesizing an intended compound having a geminal difluoro structure with a high yield from a carbonyl compound which is readily available.

DISCLOSURE OF THE INVENTION

The present inventors have conducted extensive studies to overcome the above problems and as a result, they have found a process for producing a geminal difluoro product with a high purity from a carbonyl compound by carrying out a reaction comprising two steps.

Namely, the present invention provides a process for producing a fluorine-containing compound of the following formula (2), which comprises reacting a compound of the following formula (1) with a compound of the formula X-Z or a compound of the formula $Z_2O$ (wherein Z is a monovalent group which gives a leaving group of the structure —OZ, and X is a chlorine atom, a bromine atom or an iodine atom), and then reacting a fluorinating agent which generates fluorine anions therewith to obtain the fluorine-containing compound of the following formula (2):

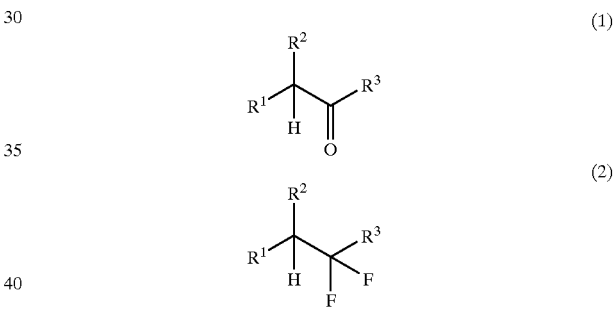

wherein each of $R^1$, $R^2$ and $R^3$ which are independent of one another, is a hydrogen atom, a fluorine atom or a monovalent organic group, or two selected from $R^1$, $R^2$ and $R^3$ together form a bivalent organic group, and the other one is a hydrogen atom, a fluorine atom or a monovalent organic group.

In the present specification, the compound of the formula (1) will be referred to as a compound (1). The same applies to compounds of other formulae. Further, the pressure in the present specification is represented by an absolute pressure.

In the present specification, a halogen atom is a fluorine atom, a chlorine atom, a bromine atom or an iodine atom. An organic group is a group which essentially has a carbon atom. A monovalent group is a group having one binding site, and it may be a monovalent organic group or a monovalent atom. A bivalent group is a group having two binding sites, and it may be a bivalent organic group or a bivalent atom.

In a case where each of $R^1$, $R^2$ and $R^3$ is a monovalent organic group, each of these groups is selected from monovalent groups which do not change by the reaction of the present invention, and preferred is a group selected from a monovalent aliphatic saturated hydrocarbon group, a monovalent aliphatic saturated hydrocarbon group substituted with a monovalent aromatic hydrocarbon group and/or a monovalent heterocyclic group, a monovalent aromatic hydrocarbon group and a monovalent heterocyclic group, a group having an ethereal oxygen atom, a thioethereal sulfur atom or a substituted nitrogen atom inserted between a carbon-carbon bond of said selected group, and an ethereal oxygen atom, a thioethereal sulfur atom or a substituted nitrogen atom bonded to the binding terminal of said selected group.

Further, at least one hydrogen atom in each of the monovalent aromatic hydrocarbon group, the monovalent aliphatic hydrocarbon group substituted with a monovalent aromatic hydrocarbon group and/or a monovalent heterocyclic group, and the monovalent heterocyclic group may be substituted with a substituent.

The substituent is preferably an alkyl group, a cycloalkyl group or the monovalent aromatic hydrocarbon group. Further, in addition to the above, preferred as the substituent is a group selected from a fluorine atom, an alkoxyl group, an alkyl-substituted amino group, a cycloalkyl-substituted amino group, an aryloxy group, an aryl-substituted amino group, —NO$_2$, —CN, —COOR$^a$, —CONR$^b$R$^c$, —SO$_2$NR$^b$R$^c$, —S(O)R$^a$, —S(O)$_2$R$^a$ and —C(OR$^a$)$_3$ (hereinafter said groups to be selected are referred to as substituent (r)).

Here, each of R$^a$, R$^b$ and R$^c$ which are independent of each other, is a C$_{1-20}$ alkyl group (such as a methyl group, an ethyl group, a 2-propyl group or a tert-butyl group), a C$_{3-8}$ cycloalkyl group (such as a cyclopropyl group, a cyclopentyl group or a cyclohexyl group), an alkyl group substituted with at least one aryl group (such as a benzyl group, a phenethyl group or a trityl group), an alkyl group substituted with at least one monovalent heterocyclic group (such as a 2-pyridylmethyl group), an aryl group (such as a phenyl group), a substituted aryl group (such as a 3-Chlorophenyl group, a 4-methylphenyl group, a 2,3-dimethoxyphenyl group, a 2-nitrophenyl group or a 4-aminophenyl group) or a fluoroalkyl group (such as —CF$_3$, —CF$_2$CF$_3$, —CH$_2$CF$_3$).

In a case where each of R$^1$, R$^2$ and R$^3$ is a monovalent organic group, preferred is an alkyl group, a cycloalkyl group, a phenyl group, an alkyl-substituted phenyl group, an alkyl-substituted monovalent heterocyclic group, a benzyl group or a group having at least one hydrogen atom in said group substituted with the above substituent (r).

Further, in a case where two selected from R$^1$, R$^2$ and R$^3$ together form a bivalent organic group (in this case, the other one group is a hydrogen atom, a fluorine atom or a monovalent organic group), preferred is a bivalent organic group selected from a bivalent saturated hydrocarbon group, a bivalent saturated hydrocarbon group containing an ethereal oxygen atom (—O—), a bivalent saturated hydrocarbon group containing a thioethereal sulfur atom (—S—) and a bivalent saturated hydrocarbon group containing —NH—, and a group having at least one hydrogen atom bonded to a carbon atom in said bivalent organic group substituted with the above substituent (r). As the bivalent saturated hydrocarbon group, an alkylene group is preferred, and a —(CH$_2$)$_n$— (wherein n is an integer of at least 1) is preferred.

As the compound (1) of the present invention, preferred is a compound wherein R$^1$ is a hydrogen atom, and R$^2$ and R$^3$ together form a tetramethylene group substituted with —COOR$^4$, particularly preferred is a compound (1a) wherein R$^1$ is a hydrogen atom, and R$^2$ and R$^3$ together form —CH$_2$CH(COOR$^4$)CH$_2$CH$_2$—. Further, as the fluorine-containing compound (2) as an intended compound of the present invention, preferred is the following fluorine-containing compound (2a) corresponding to the compound (1a). Further, as intermediates (3) to (7) as described hereinafter, preferred are compounds wherein R$^1$ is a hydrogen atom, and R$^2$ and R$^3$ together form a tetramethylene group substituted with —COOR$^4$ (particularly a group —CH$_2$CH(COOR$^4$)CH$_2$CH$_2$—).

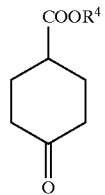

(1a)

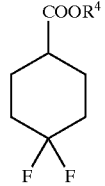

(2a)

wherein R$^4$ is a group similar to the above R$^a$, it is a C$_{1-20}$ alkyl group, a C$_{3-8}$ cycloalkyl group, an alkyl group substituted with at least one aryl group, an alkyl group substituted with at least one monovalent heterocyclic group, an aryl group, a substituted aryl group or a C$_{1-20}$ fluoroalkyl group, preferably a methyl group, an ethyl group, a phenyl group, a benzyl group, a propyl group, an isopropyl group, a butyl group, a tert-butyl group, a hexyl group, a cyclohexyl group or a substituted phenyl group, particularly preferably a C$_{1-20}$ alkyl group or a C$_{3-8}$ cycloalkyl group. A compound (1a) wherein R$^4$ is methyl or ethyl is a known compound, and is a compound available as a commercially available product or by a known production method. Another compound (1a) can be derived from the known compound.

In the present invention, first, the compound (1) is reacted with a compound of the formula X-Z (hereinafter referred to as compound A) or a compound of the formula Z$_2$O (hereinafter referred to as compound B).

Z in the compound A is a monovalent group which gives a leaving group of the structure —OZ. —OZ is a leaving group which leaves and is substituted with a fluorine atom in a reaction with a fluorinating agent of the present invention. Z may, for example, be a hydrogen atom (—OH is a leaving group), —POCl$_2$ (—OP(O)Cl$_2$ is a leaving group) or a —COCH$_3$ (—OCOCH$_3$ is a leaving group). X in the compound A (X-Z) is a chlorine atom, a bromine atom or an iodine atom. X is substituted with a fluorine atom in the reaction with a fluorinating agent. X in the compound A is preferably a chlorine atom.

The compound A is preferably a compound represented by HX, POX$_3$, PX$_5$, SOX$_2$, SO$_2$X$_2$, (COX)$_2$, R$^5$COX, R$^5$SO$_2$X or (R$^5$O)$_3$P(O)X. R$^5$ is a monovalent organic group, and preferably a group selected from an alkyl group, a halogenated alkyl group, an aryl group, an alkyl-substituted aryl group, an aryl-substituted alkyl group or an (alkyl-substituted aryl)alkyl group.

Among them, more preferred as the compound A is a compound represented by POX$_3$, PX$_5$, SOX$_2$, (COX)$_2$, CH$_3$COCl, PhCOCl (wherein Ph is a phenyl group, the same applies hereinafter), CH$_3$CH$_2$COCl, p-CH$_3$C$_6$H$_4$SO$_2$Cl (wherein C$_6$H$_4$ is a phenylene group), CH$_3$SO$_2$Cl, CF$_3$SO$_2$Cl, (PhO)$_2$PO-X, (CH$_3$CH$_2$O)$_2$PO-X or (CH$_3$O)$_2$PO-X, and PX$_5$ is particularly preferred from such a reason that treatment after the reaction is readily carried out. These compounds A are readily available compounds.

Z in the compound B ($Z_2O$) may be a group similar to Z in the compound A. As the compound B, preferred is ($R^5CO)_2O$ or ($R^5SO_2)_2O$ (wherein $R^5$ is as defined above), particularly preferred is ($CH_3CO)_2O$, ($PhCO)_2O$ or ($CF_3SO_2)_2O$.

In the present invention, the compound (1) is reacted with the compound A or the compound B (hereinafter this reaction step will be referred to as a first step). The product in the first step reaction (hereinafter referred to as an intermediate) varies depending upon e.g. the structure of the compound (1) used for the reaction, the structure of the compound A or the compound B and reaction conditions. In the present invention, such an intermediate may be isolated as the case requires, but the intermediate is introduced to an intended fluorine-containing compound (2) even when a fluorination reaction in the subsequent second step is carried out without isolating the intermediate.

In a usual case, in the reaction of the compound (1) with the compound A, at least one type of a compound selected from compounds (3) to (7) may form as an intermediate. $R^1$, $R^2$, $R^3$, X and Z in the following formulae (3) to (7) correspond to the compound A used for the reaction. In the present invention, the second step may be carried out after the formed intermediate is taken out, or the second step may be carried out without taking such a compound out. Said intermediate may be one type or at least two types, and at least two types are formed in a usual case.

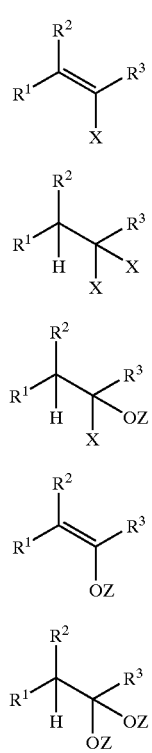

As compounds (3) to (7), compounds (3a) to (7a), respectively, are preferred. X, Z and $R^4$ in the following formulae-are as defined above, and preferred embodiments are also as described above.

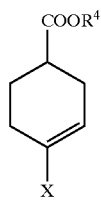

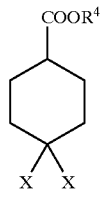

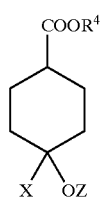

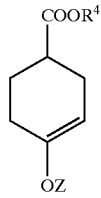

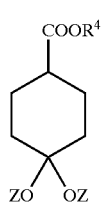

On the other hand, in the reaction of the compound (1) with the compound B, usually a compound (6) and/or a compound (7) forms as an intermediate. $R^1$, $R^2$, $R^3$ and Z in the following formulae (6) and (7) correspond to the compound B used for the reaction. In the present invention, the formed intermediate may be taken out and then introduced to the second step, or the fluorination reaction may be carried out without taking such a compound out. The intermediate may be one type or two types, and in a usual case, at least two types of compounds are preferably formed.

The intermediate when the compound (1a) is reacted with the compound B, preferred is at least one type of a compound selected from the compound (6a) and the compound (7a), and usually the compound (6a) and the compound (7a) are preferred. Z and $R^4$ in the formulae are as defined above, and the preferred embodiments are as described above.

The above compounds (3) to (7), particularly the compounds (3a) to (7a) are compounds having boiling points close to one another, and they are respectively unstable compounds, and accordingly it tends to be difficult to separate them by a conventional separation and purification operation. However, according to the process of the present invention, even if at least two types of intermediates are formed, they do not have to be taken out, and can be directly used to the subsequent second step.

It is not necessary to isolate the formed intermediates, but it is preferred to carry out an after-treatment which is carried out after a usual reaction. As a method of the after-treatment, distillation of the reaction solvent, extraction with a solvent, washing with an acid or alkali aqueous solution and/or water, crystallization or column chromatography purification may, for example, be mentioned.

The amounts of the compound A and the compound B used for the reaction are usually preferably from 0.1 to 100 times the molar quantity of the compound (1), particularly preferably from 1.0 to 10 times the molar quantity. The reaction temperature is usually preferably from −50 to 250° C. in view of e.g. handling efficiency, particularly preferably within a range of from −20 to 200° C. The reaction time is usually preferably from 0.1 to 72 hours, particularly preferably from 0.5 to 48 hours. The reaction pressure is optionally changed depending upon the reaction temperature, and the reaction is carried out preferably by a liquid phase reaction, and thus it is preferably from 0.01 MPa to 10.00 MPa, more preferably from 0.08 MPa to 3.00 MPa.

The first step reaction may be carried out in the presence of a solvent. As the solvent, one type or at least two types of solvents inert in the reaction may be employed. As the solvent, a hydrocarbon type solvent such as toluene, xylene, benzene, cyclohexane or n-hexane, a halogenated hydrocarbon type solvent such as dichloromethane, dichloroethane, carbon tetrachloride, chloroform, chlorobenzene or 1,2-dichlorobenzene, an ester type solvent such as ethyl acetate or n-butyl acetate, an ether type solvent such as diethyl ether, diisopropyl ether, methyl tert-butyl ether, ethylene glycol dimethyl ether, tetrahydrofuran or dioxane, a nitrile type solvent such as acetonitrile, an amide type solvent such as N,N-dimethylformamide, N,N-dimethylacetamide, N-methylpyrrolidone or N-methylpyrrolidinone, or dimethylsulfoxide, phosphorus oxychloride or water may, for example, be mentioned.

As the solvent, preferred are e.g. ethyl acetate, acetonitrile, dichloromethane, chloroform, chlorobenzene, 1,2-dichlorobenzene, methyl tert-butyl ether, dimethylsulfoxide, dimethylformamide, phosphorus oxychloride, hexane, toluene or xylene. When a solvent is used, its amount is preferably from 0.5 to 200 mL per 1 g of the compound (1) from such a reason as readiness in the after-treatment, particularly preferably from 1 to 50 mL.

The first step reaction may be carried out in the presence of a base. The base may be an organic base or an inorganic base. The organic base may, for example, be triethylamine, diisopropylethylamine, pyridine, 4-dimethylaminopyridine, morpholine, 1,5-diazabicyclo[4.3.0]nona-5-ene, 1,8-diazabicyclo[5.4.0]undeca-7-ene, sodium methoxide or potassium tert-butoxide. The inorganic base may, for example, be an alkali metal hydroxide such as sodium hydroxide, potassium hydroxide or lithium hydroxide, an alkaline earth metal hydroxide such as calcium hydroxide or magnesium hydroxide, an alkali metal carbonate such as sodium carbonate or potassium carbonate, an alkali metal hydrogencarbonate such as sodium hydrogencarbonate or potassium hydrogencarbonate, or an alkali metal hydride such as sodium hydride.

In a case where a base is employed, its amount is usually preferably from 0.1 mol to 200 mol per 1 mol of the compound (1), particularly preferably from 0.2 mol to 100 mol.

Then, in the present invention, a reaction with a fluorinating agent (hereinafter this reaction step will be referred to as the second step) is carried out. In the second step, even if at least two types of the intermediates are formed in the first step, they are used without being separated. Further, in a case where at least two types of products are formed in the first step, their proportion and the like are not particularly limited and they may be used for the second step.

The second step is a reaction with a fluorinating agent, and the fluorinating agent in the present invention causes a fluorination reaction by the action of fluorine anions. The fluorinating agent which generates fluorine anions in the second step may, for example, be HF, pyridinium polyhydrogen fluoride, tetrabutylammonium dihydrogen trifluoride, tetrabutylammonium fluoride, $AgF_2$, $SbF_5$, $SbF_3$, $SbF_3Cl_2$, $CrF_3$, $HgF$, $HgF_2$, $RbF$, $KF$, $NaF$, $LiF$, $KSO_2F$, $KHF_2$, $ZnF_2$, $CaF_2$, $CsF$, $Na_2SiF_6$, $AsF_3$, $BrF_3$, $IF_5$, $IF_7$, $NbF_5$ or $TaF_5$. Among them, preferred is HF or KF since they are available at a low cost, and the after-treatment is readily carried out with them, and HF is particularly preferred.

The amount of the fluorinating agent is usually preferably from 0.1 to 100 times the molar quantity of the total number of mols of the product in the first step, particularly preferably from 0.2 to 50 times the molar quantity, with respect to the fluorinating agent other than HF. In the case of HF, its amount is preferably from 0.1 to 500 times by mass the total mass of the product in the first step, particularly preferably from 0.5 to 100 times by mass.

The reaction temperature in the second step is usually preferably from −50 to 250° C. in view of e.g. operation efficiency, particularly preferably from −20 to 200° C. The reaction temperature is not necessarily constant, and is preferably optionally adjusted depending upon the progress of the reaction. The reaction time in the second step is usually preferably from 0.1 to 72 hours, particularly preferably from 0.5 to 48 hours. The reaction pressure is optionally changed depending upon the reaction temperature, and it is preferably from 0.01 MPa to 10.0 MPa, particularly preferably from 0.08 MPa to 3.00 MPa, especially preferably the pressure in the vicinity of normal pressure, from such a reason that the reaction can be carried out as a liquid phase reaction. Further, in a case where hydrogen chloride is generated in the reaction, the reaction system is preferably at least 0.01 MPa, particularly preferably from 0.1 MPa to 0.5 MPa, from such a reason that hydrogen chloride is occasionally removed, whereby the fluorination reaction is accelerated. The second step reaction is carried out preferably by using a reaction vessel made of hastelloy or a reaction vessel having the inner surface lined with a fluororesin.

The second step reaction may be carried out in the presence of a catalyst. The catalyst is preferably a Lewis acid catalyst. As the Lewis acid catalyst, the following compounds may be mentioned. The halogen atom in the following metal halides may be one type or at least two types, and is preferably a bromine atom, a chlorine atom or an iodine atom.

The Lewis acid catalyst may, for example, be an alkali metal halide, an alkaline earth metal halide, a transition metal halide, silane halide, germanium halide, boron halide, aluminum halide, gallium halide, indium halide, thallium halide, tin halide, titanium halide, lead halide, bismuth halide, antimony halide, tellurium halide, selenium halide, germanium halide, niobium halide, $IF_3$, $BF_3$ or a metal oxide, and preferred are antimony(III) halide, antimony(V) halide, aluminum(III) halide, chromium(III) halide, silver(I) halide, mercury(I) halide, mercury(II) halide, calcium(II) halide, boron(III) halide, arsenic(III) halide, magnesium(II) halide, beryllium(II) halide, niobium(V) halide, thallium(V)

halide, rubidium(III) halide, tin(IV) halide, titanium(IV) halide, aluminum oxide and vanadium oxide. Among them, e.g. $SbF_5$, $SbCl_5$, $SbCl_2F_3$, $NbCl_5$, $NbClF_4$, $NbF_5$, $TaF_5$, $TaCl_5$ and $TaClF_4$ may be mentioned as preferred examples, since their reactivity is high.

The amount of the Lewis acid catalyst is usually preferably from 0.1 to 100 mol % based on the compound (1), particularly preferably from 0.2 to 50 mol %. Further, the catalyst may be added after the fluorinating agent and the product in the first step are mixed, or the catalyst may be added to the fluorinating agent, and then the product in the first step is added thereto.

The second step reaction may be carried out in the presence of a solvent. The solvent may optionally be selected from solvents inert in the fluorination reaction. One type or at least two types of the solvents may be used.

The solvent may, for example, be a hydrocarbon type solvent such as toluene, xylene, benzene, cyclohexane or n-hexane, a chlorofluorocarbon type solvent or a fluorocarbon type solvent such as HFC-134a, HCFC-22, HCFC-124, HFC-125, HFC-32, HFC-134, HCFC-123, HCFC-124 or HCFC-225, an ether type solvent such as diethyl ether, diisopropyl ether, methyl tert-butyl ether, ethylene glycol dimethyl ether, tetrahydrofuran or dioxane, an ester type solvent such as ethyl acetate or n-butyl acetate, a cyano type solvent such as acetonitrile, an amide type solvent such as N,N-dimethylformamide, N,N-dimethylacetamide, N-methylpyrrolidone or N-methylpyrrolidinone, a halogenated aromatic hydrocarbon type solvent such as dichlorobenzene or chlorobenzene, or dimethylsulfoxide or water.

Among them, as the solvent in the second step, preferred is e.g. ethyl acetate, acetonitrile, dimethylsulfoxide, dimethylformamide, hexane, toluene, xylene, dioxane or HCFC-225. Further, in a case where a solvent is used, its amount is preferably from 0.1 to 200 mL per 1 g of the product in the first step, in view of e.g. the after-treatment, particularly preferably from 1 to 50 mL.

In the production process of the present invention, a fluorine-containing compound (2) having a geminal difluoro structure is obtained. $R^1$, $R^2$ and $R^3$ in the fluorine-containing compound (2) correspond to those in the compound (1) and are as defined above. The reaction crude product containing the formed fluorine-containing compound (2) is preferably subjected to an after-treatment depending upon the purpose. As a method of the after-treatment, a method of the after-treatment similar to that in the case of the first step may be mentioned, and distillation is preferred. Particularly when HF is used as a fluorinating agent, it is preferred to vaporize and remove excess HF as far as possible, followed by neutralization to remove HF, and to carry out the after-treatment.

The fluorine-containing compound (2) obtained by the production process of the present invention is a compound useful as perfume, pharmaceuticals, agricultural chemicals and chemical agents, or as intermediates therefor. Particularly, the fluorine-containing compound (2a) is a compound useful as an intermediate for pharmaceuticals and agricultural chemicals.

BEST MODE FOR CARRYING OUT THE INVENTION

Now, the present invention will be explained with reference to Examples, but the present invention is not limited thereto.

EXAMPLE 1

Example for First Step Reaction

Phosphorus pentachloride (136 g, 0.65 mol) and 325 mL of toluene were mixed in an atmosphere of nitrogen, and while keeping the temperature to be within a range of from 0 to 10° C. by cooling with ice water, ethyl 4-oxocyclohexanecarboxylate (111 g, 0.65 mol) was dropwise added thereto over a period of 30 minutes. The solid part gradually dissolved from the initial suspended state, and the suspension became a completely clear solution in the middle of the dropwise addition. After completion of the dropwise addition, stirring was continued for 10 minutes, and disappearance of the material was confirmed by gas chromatography. A distillation apparatus was attached to a reaction flask, and at least half the content (369 g) was distilled off under reduced pressure. 190 g of an oily substance remaining in the flask was diluted with toluene, washed with 200 mL of water, 50 mL of an aqueous sodium chloride solution and 50 mL of water, and dried over magnesium sulfate and concentrated by an evaporator, and further dried under reduced pressure in vacuum to obtain 146 g of a redish brown oily substance. The redish brown oily substance contained ethyl 4-chloro-3-cyclohexenecarboxylate, ethyl 4,4-dichlorocyclohexanecarboxylate and toluene in amounts of 52%, 28% and 20%, respectively.

EXAMPLE 2

Example for Second Step Reaction

Anhydrous hydrogen fluoride (60 g, 3 mol) was introduced to a 200 mL hastelloy autoclave under reduced pressure, and antimony pentachloride (3 g, 0.01 mol) was added thereto under nitrogen pressure of 0.5 MPa, followed by stirring at room temperature for 1 hour (234 rpm). During this stirring, the internal pressure increased from 0.15 MPa to 0.17 MPa. In such a state, the above chlorinated product (18.8 g, 75.2 mmol) was added thereto dividedly in three times under a nitrogen pressure of 0.6 MPa, whereupon the internal pressure became 0.3 MPa, and the internal temperature increased from 14° C. to 21° C. Stirring was carried out at room temperature for 1 hour, whereupon the internal temperature decreased to 16° C., and the internal pressure increased to 0.32 MPa. The autoclave was heated over a period of 30 minutes until the internal temperature become 50° C., and heating was carried out for 1 hour. A needle valve was opened when the internal pressure became 0.4 MPa to decrease the internal pressure to 0.3 MPa, and this operation was repeatedly carried out totally 6 times. After no increase in the internal pressure was observed, the autoclave was heated to 50° C. to eject excess hydrogen fluoride, and the autoclave was opened, and the content was added to a potassium hydrogencarbonate aqueous solution cooled with ice. After extraction with ethyl acetate, the organic layer was washed with water, dried over magnesium sulfate and concentrated by an evaporator to obtain 15.13 g of blackish brown oily substance. The oily substance was distilled off under reduced pressure to obtain ethyl 4,4-difluorocyclohexanecarboxylate (2 g, purity of at least 99% as calculated from peak area by gas chromatography).

$^1$H-NMR δ (ppm): 1.26 (3H, t), 1.7 to 2.5 (9H, m), 4.14 (2H, q).

$^{19}$F-NMR δ (ppm): −94.9 (d), −100.1 (d)

INDUSTRIAL APPLICABILITY

According to the production process of the present invention, a fluorine-containing compound having a geminal difluoro structure can be produced efficiently and positionselectively, employing a carbonyl compound which is readily available as a material by a two-step reaction. In the process of the present invention, even if at least two types of intermediates are formed in the first step, it is possible to carry out the subsequent step without separating them, and a fluorine-containing compound with a high purity can be obtained from the product in the second step. Accordingly, a fluorine-containing compound with a high purity can be obtained without carrying out a complicated separation operation in the process of the production steps or on the product. Further, the fluorination reaction may be carried out by using e.g. HF, such being advantageous since the production cost can be decreased as compared with a conventional method, and this process can be an industrially useful production process.

The entire disclosure of Japanese Patent Application No. 2001-024174 filed on Jan. 31, 2001 including specification, claims and summary is incorporated herein by reference in its entirety.

What is claimed is:

1. A process for producing a fluorine-containing compound of the following formula (2), which comprises reacting a compound of the following formula (1) with a compound of the formula X-Z or a compound of the formula $Z_2O$ (wherein Z is a monovalent group which gives a leaving group of the structure —OZ, and X is a chlorine atom, a bromine atom or an iodine atom), and then further reacting with a fluorinating agent which generates fluorine anions thereon to obtain the fluorine-containing compound of the following formula (2):

(1)

(2)

wherein each of $R^1$, $R^2$ and $R^3$ which are independent of one another, is a hydrogen atom, a fluorine atom or a monovalent organic group, or two selected from $R^1$, $R^2$ and $R^3$ together form a bivalent organic group, and the other one is a hydrogen atom, a fluorine atom or a monovalent organic group.

2. The production process according to claim 1, wherein the fluorinating agent which generates fluorine anions is HF.

3. The production process according to claim 1, wherein the fluorinating agent which generates fluorine anions reacts in the presence of a catalyst.

4. The production process according to claim 1, wherein the compound of the formula (1) is a compound of the following formula (1a), and the fluorine containing compound of the formula (2) is a fluorine-containing compound of the following formula (2a):

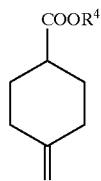
(1a)

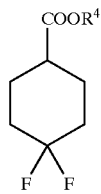
(2a)

wherein $R^4$ is a $C_{1-20}$ alkyl group, a $C_{3-8}$ cycloalkyl group, an alkyl group substituted with at least one aryl group, an alkyl group substituted with at least one monovalent heterocyclic group, an aryl group, a substituted aryl group or a $C_{1-20}$ fluoroalkyl group.

5. The production process according to claim 1, wherein the compound formed by the reaction of the compound of the formula (1) with the compound of the formula X-Z or the compound of the formula $Z_2O$ comprises at least two types of compounds, and the fluorinating agent which generates fluorine atoms reacts with said at least two types of compounds without isolating them.

6. A process for producing a fluorine-containing compound of the following formula (2), which comprises reacting a compound of the following formula (1) with a compound X-Z (wherein Z is a monovalent group which gives a leaving group of the structure —OZ, and X is a chlorine atom, a bromine atom or an iodine atom) to obtain at least one type of a compound selected from compounds of the following formulae (3) to (7), and then reacting a fluorinating agent which generates fluorine anions with said at least one type of a compound to obtain the fluorine-containing compound of the following formula (2):

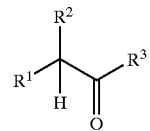
(1)

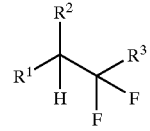
(2)

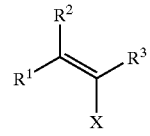
(3)

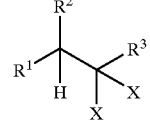
(4)

-continued

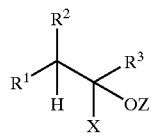

(5)

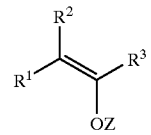

(6)

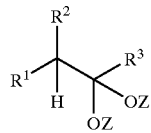

(7)

wherein each of $R^1$, $R^2$ and $R^3$ which are independent of one another, is a hydrogen atom, a fluorine atom or a monovalent organic group, or two selected from $R^1$, $R^2$ and $R^3$ together form a bivalent organic group, and the other one is a hydrogen atom, a fluorine atom or a monovalent organic group.

7. The production process according to claim 6, wherein the fluorinating agent which generates fluorine anions is HF.

8. The production process according to claim 6, wherein the fluorinating agent which generates fluorine anions reacts in the presence of a catalyst.

9. The production process according to claim 6, wherein the compound of the formula (1) is a compound of the following formula (1a), and the fluorine containing compound of the formula (2) is a fluorine-containing compound of the following formula (2a):

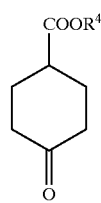

(1a)

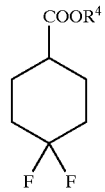

(2a)

wherein $R^4$ is a $C_{1-20}$ alkyl group, a $C_{3-8}$ cycloalkyl group, an alkyl group substituted with at least one aryl group, an alkyl group substituted with at least one monovalent heterocyclic group, an aryl group, a substituted aryl group or a $C_{1-20}$ fluoroalkyl group.

10. The production process according to claim 6, wherein the compound formed by the reaction of the compound of the formula (1) with the compound of the formula X-Z or the compound of the formula $Z_2O$ comprises at least two types of compounds, and the fluorinating agent which generates fluorine atoms reacts with said at least two types of compounds without isolating them.

11. A process for producing a fluorine-containing compound of the following formula (2), which comprises reacting a compound of the following formula (1) with a compound of the formula $Z_2O$ (wherein Z is a monovalent group which gives a leaving group of the structure —OZ) to obtain at least one type of a compound selected from a compound of the following formula (6) and a compound of the following formula (7), and then reacting a fluorinating agent which generates fluorine anions with said at least one type of the compound to obtain the fluorine-containing compound of the following formula (2):

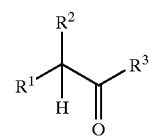

(1)

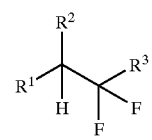

(2)

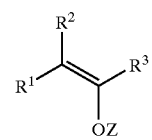

(6)

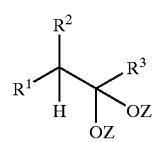

(7)

wherein each of $R^1$, $R^2$ and $R^3$ which are independent of one another, is a hydrogen atom, a fluorine atom or a monovalent organic group, or two selected from $R^1$, $R^2$ and $R^3$ together form a bivalent organic group, and the other one is a hydrogen atom, a fluorine atom or a monovalent organic group.

12. The production process according to claim 11, wherein the fluorinating agent which generates fluorine anions is HF.

13. The production process according to claim 11, wherein the fluorinating agent which generates fluorine anions reacts in the presence of a catalyst.

14. The production process according to claim 11, wherein the compound of the formula (1) is a compound of the following formula (1a), and the fluorine containing compound of the formula (2) is a fluorine-containing compound of the following formula (2a):

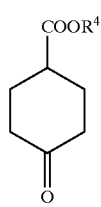

(1a)

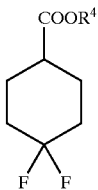

(2a)

wherein $R^4$ is a $C_{1-20}$ alkyl group, a $C_{3-8}$ cycloalkyl group, an alkyl group substituted with at least one aryl group, an alkyl group substituted with at least one monovalent heterocyclic group, an aryl group, a substituted aryl group or a $C_{1-20}$ fluoroalkyl group.

15. The production process according to claim 11, wherein the compound formed by the reaction of the compound of the formula (1) with the compound of the formula X-Z or the compound of the formula $Z_2O$ comprises at least two types of compounds, and the fluorinating agent which generates fluorine atoms reacts with said at least two types of compounds without isolating them.

16. The production process according to claim 1, wherein the compound of formula (1) is reacted with the compound of formula X-Z, which compound of formula X-Z is selected from the group consisting of HX, $POX_3$, $PX_5$, $SOX_2$, $SO_2X_2$, $(COX)_2$, $R^5COX$, $R^5SO_2X$ and $(R^5O)_3P(O)X$, wherein $R^5$ is a monovalent organic group.

17. The production process according to claim 16, wherein the compound of formula X-Z is selected from the group consisting of $POX_3$, $PX_5$, $SOX_2$, $(COX)_2$, $CH_3COCl$, $PhCOCl$, $CH_3CH_2COCl$, p-$CH_3C_6H_4SO_2Cl$, $CH_3SO_2Cl$, $CF_3SO_2Cl$, $(PhO)_2PO$-X, $(CH_3CH_2O)_2PO$-X and $(CH_3O)_2PO$-X, wherein Ph is a phenyl group.

18. The production process according to claim 17, wherein the compound of formula X-Z is $PX_5$.

19. The production process according to claim 1, wherein the compound of formula (1) is reacted with a compound of formula $Z_2O$, which compound of formula $Z_2O$ is $(R^5CO)_2O$ or $(R^5SO_2)_2O$, wherein $R^5$ is a monovalent organic group.

20. The production process according to claim 19, wherein the compound of formula $Z_2O$ is $(CH_3CO)_2O$, $(PhCO)_2O$ or $(CF_3SO_2)_2O$, wherein Ph is a phenyl group.

* * * * *